United States Patent [19]

Paley

[11] 4,432,392
[45] * Feb. 21, 1984

[54] PLASTIC MANIFOLD ASSEMBLY

[76] Inventor: Hyman W. Paley, 25 Broadmoor Dr., San Francisco, Calif. 94132

[*] Notice: The portion of the term of this patent subsequent to Dec. 11, 1996 has been disclaimed.

[21] Appl. No.: 43,452

[22] Filed: May 29, 1979

Related U.S. Application Data

[63] Continuation of Ser. No. 727,791, Sep. 29, 1976, Pat. No. 4,177,835.

[51] Int. Cl.³ .............................................. E03B 7/07
[52] U.S. Cl. .................................. 137/883; 137/343; 137/887
[58] Field of Search .................. 137/625, 47, 883, 887, 137/343; 251/287, 309, 312

[56] References Cited

U.S. PATENT DOCUMENTS

| 262,935 | 8/1882 | Dibble | 251/317 |
| 1,493,133 | 5/1924 | Sykora | 137/625.47 |
| 2,751,930 | 6/1956 | Redner | 251/317 |
| 3,019,815 | 2/1962 | Lenardon et al. | 137/883 |
| 3,154,102 | 10/1964 | Harris | 137/883 |
| 3,192,943 | 7/1965 | Moen | 251/288 |
| 3,447,469 | 11/1969 | Paley | 137/883 |
| 3,451,652 | 6/1969 | Watson | 251/317 |
| 3,459,221 | 8/1969 | Axelrod | 137/883 |
| 3,499,464 | 3/1970 | Williams et al. | 137/883 |
| 3,643,694 | 2/1972 | Duke et al. | 137/883 |

FOREIGN PATENT DOCUMENTS 402689 10/1909 France ............................ 251/287

Primary Examiner—Martin P. Schwadron
Attorney, Agent, or Firm—Flehr, Hohbach, Test, Albritton & Herbert

[57] ABSTRACT

Manifold assembly having a plastic body with intersect flow passages and valve members for controlling communication between the passageways. Stops limit the movement of the valve members between predetermined positions, and the valve members can be removed from the body and reinstalled in reversed position to provide fixed communication between certain of the passageways. Externally threaded nipples are provided for connecting the assembly to external fixtures, and resilient sleeves are inserted between the valve members and the body to form fluid tight seals.

8 Claims, 22 Drawing Figures

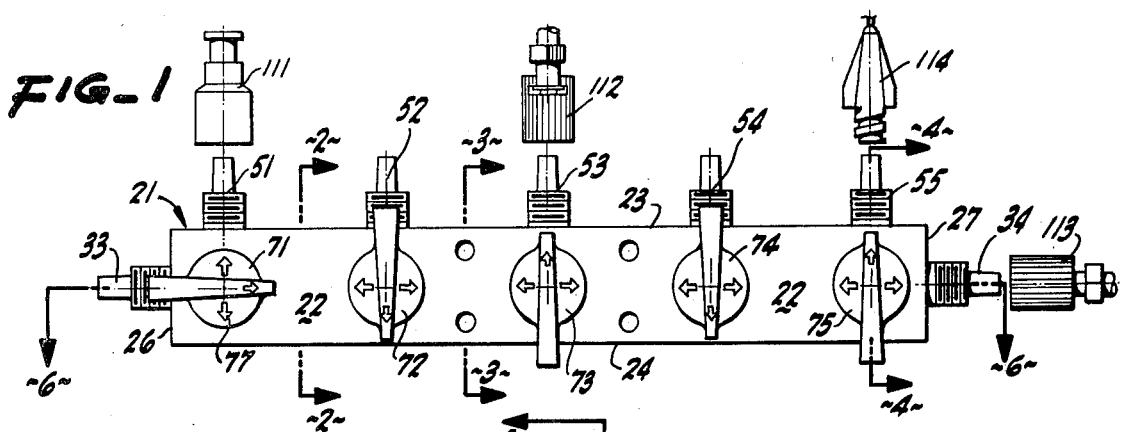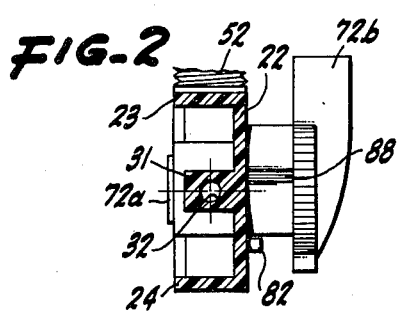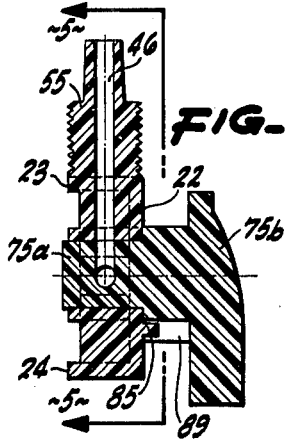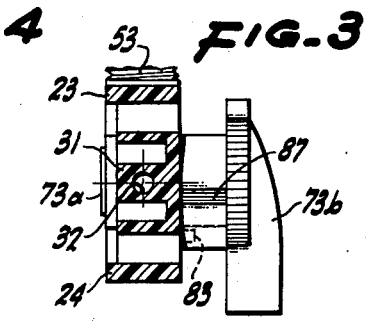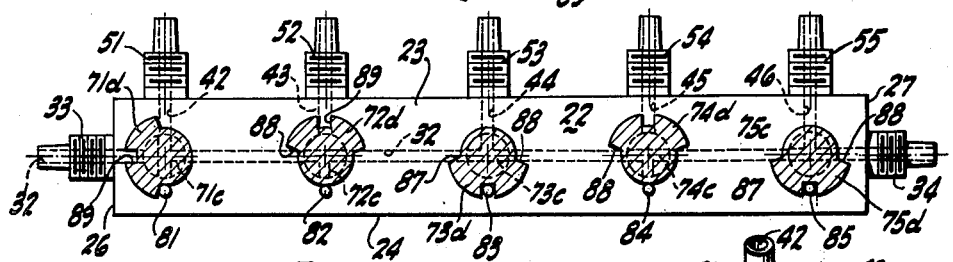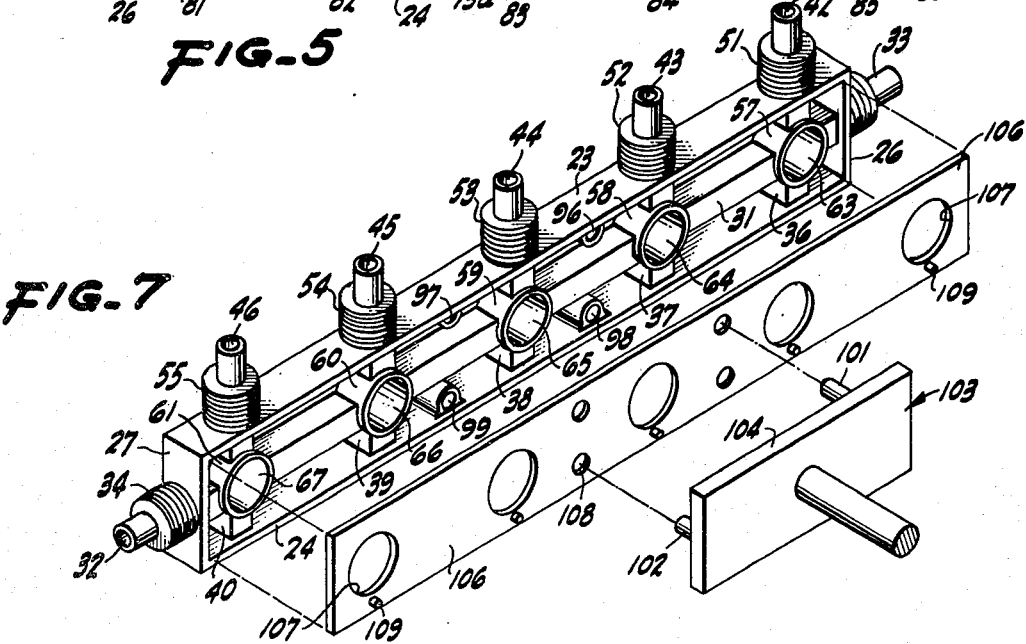

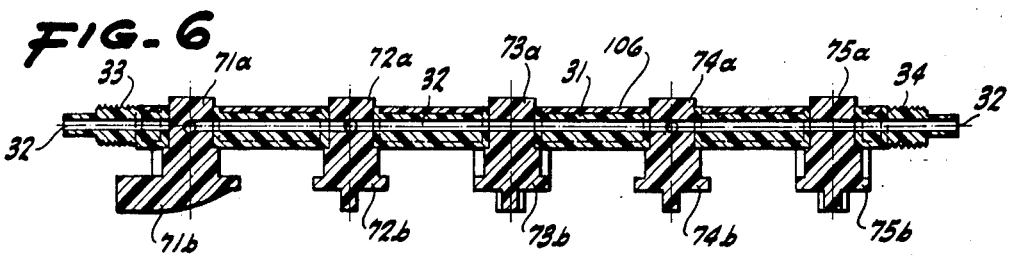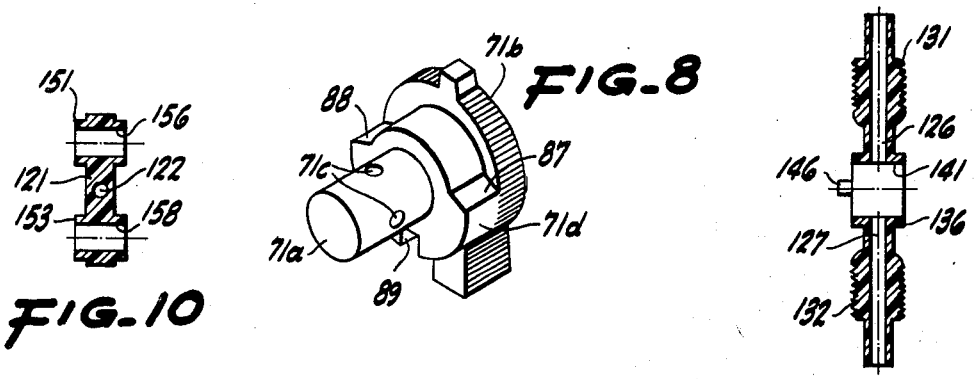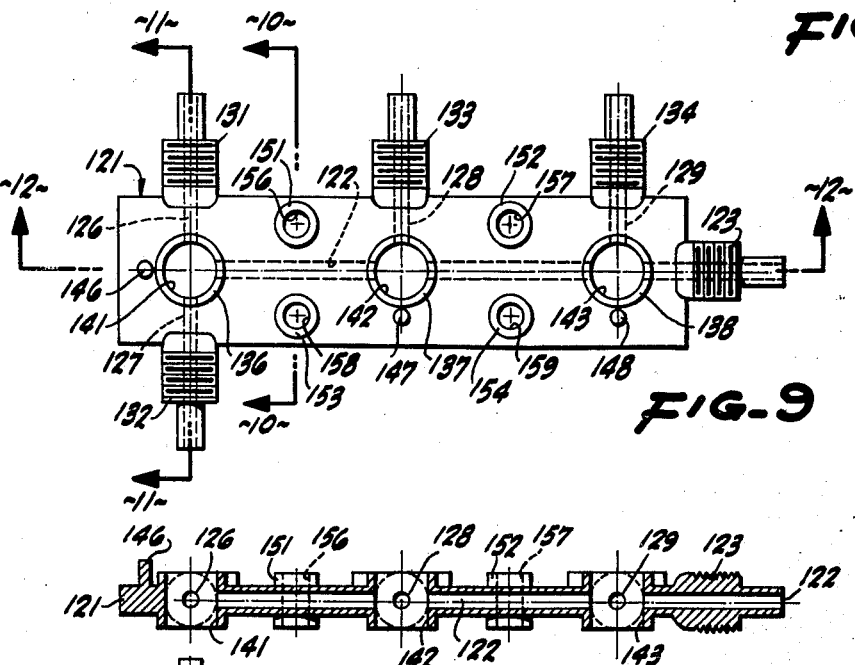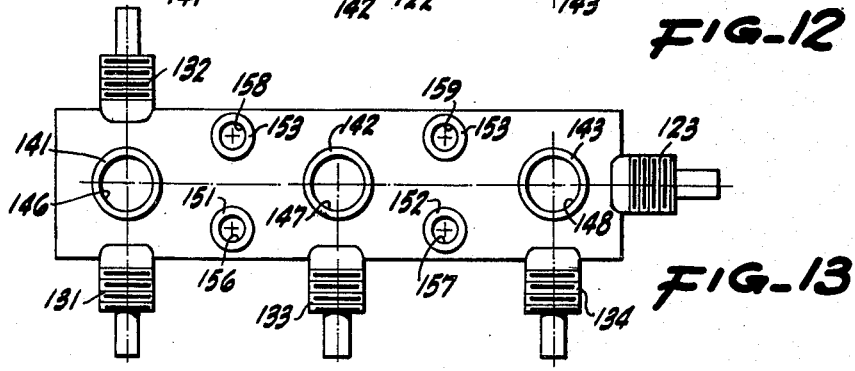

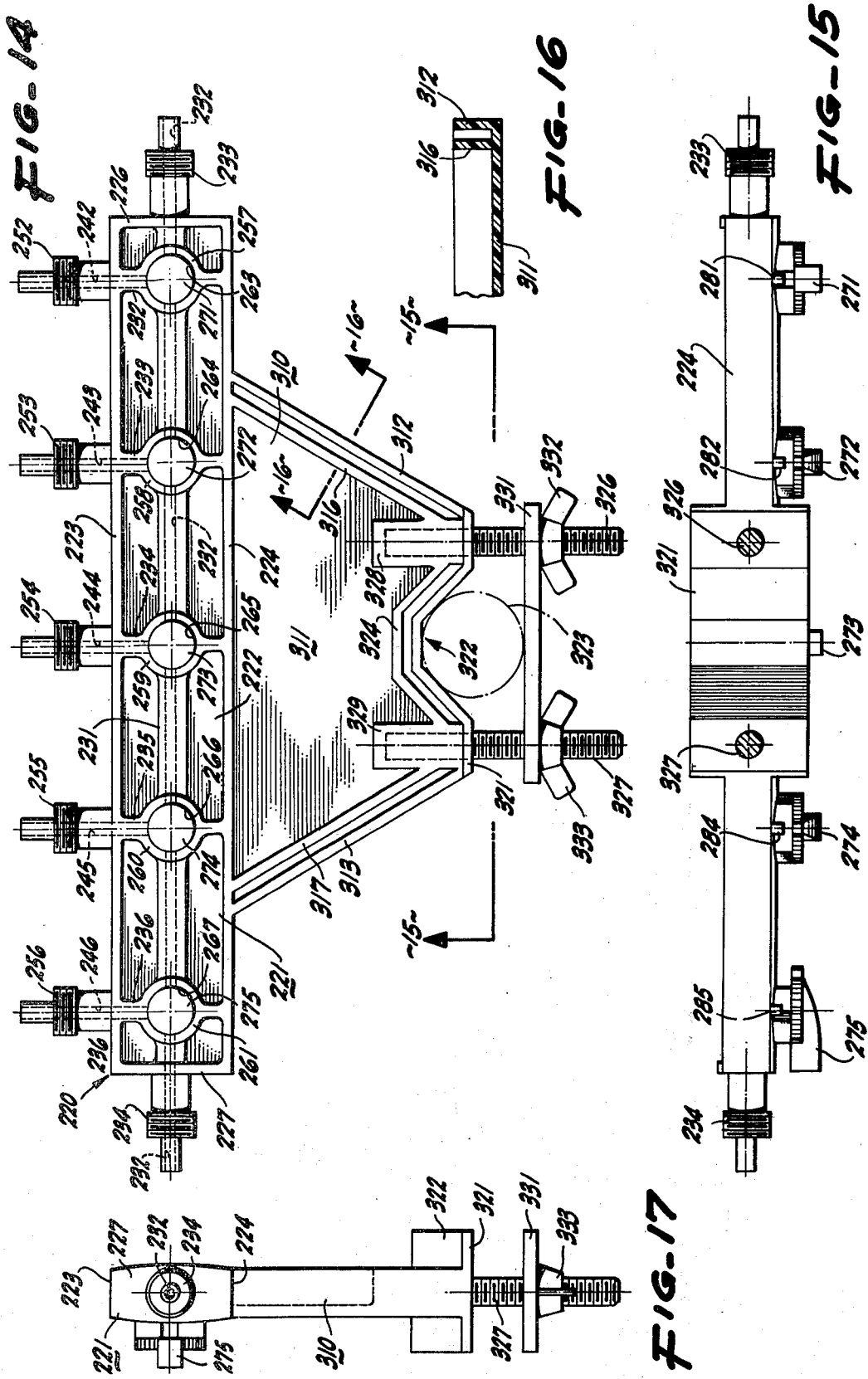

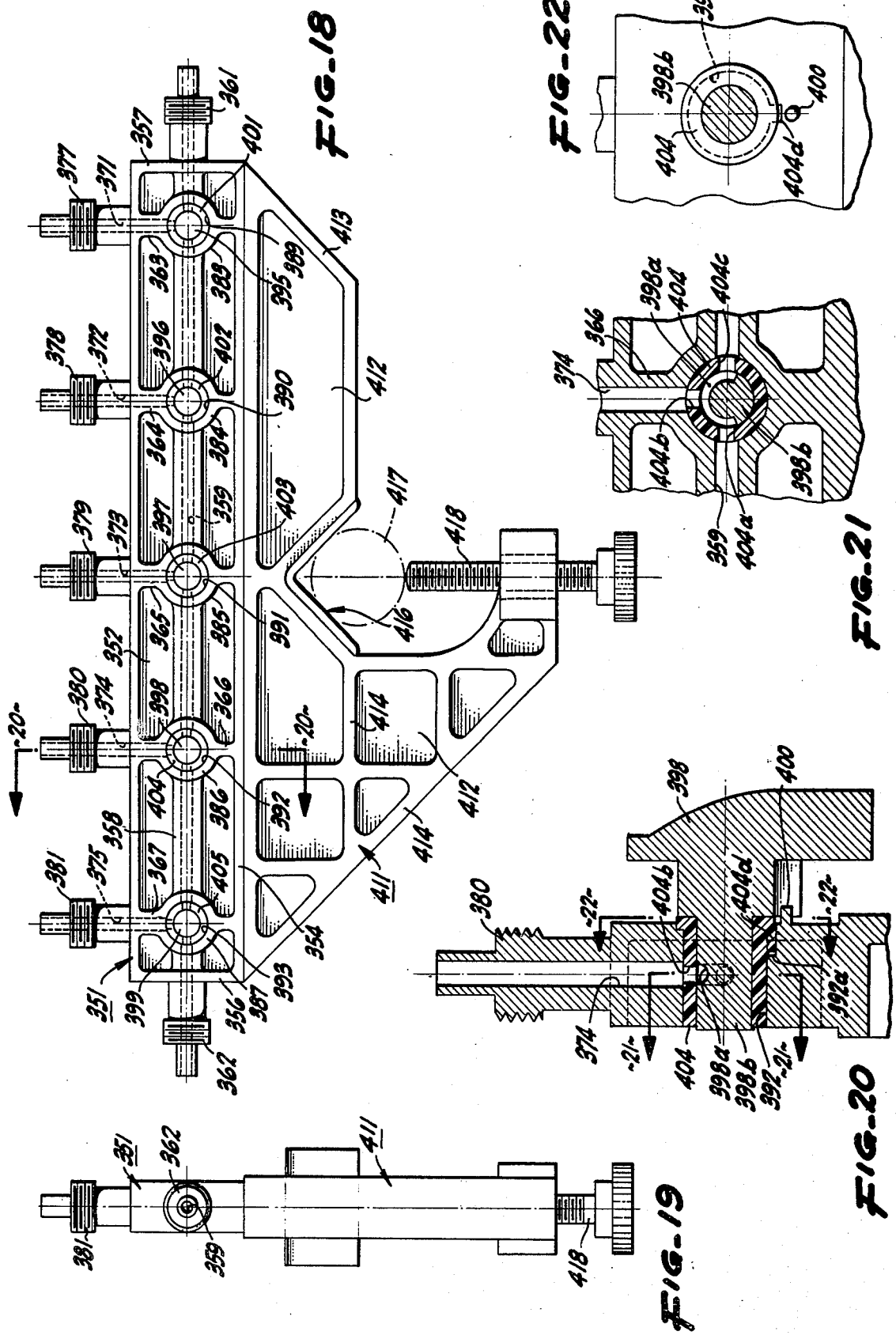

4,432,392

PLASTIC MANIFOLD ASSEMBLY

CROSS REFERENCE TO RELATED APPLICATIONS

This is a continuation of Application Ser. No. 727,791, filed Sept. 29, 1976, now U.S. Pat. No. 4,177,835, a continuation of Application Ser. No. 579,906, filed May 22, 1975, now abandoned, a continuation-in-part of Ser. No. 538,936, filed Jan. 6, 1975, now abandoned.

BACKGROUND OF THE INVENTION

This invention pertains generally to medical appliances and more particularly to a manifold assembly for controlling flows of fluid and pressure.

Manifold assemblies have been provided in the past for medical applications, and one such assembly is shown in U.S. Pat. No. 3,477,469, issued Nov. 11, 1969 to the applicant herein. These prior art manifolds are commonly made of stainless steel, and while they have been found to give reliable performance for long periods of time, they require substantial machining and therefore are expensive to manufacture.

SUMMARY AND OBJECTS OF THE INVENTION

The invention provides a plastic manifold assembly which can be manufactured by a relatively inexpensive molding process, with the reliability and durability heretofore associated with the more expensive stainless steel manifolds. This assembly comprises a plastic body having intersecting flow passageways and valve members for controlling communication between the passageways. Stops limit the movement of the valve members between predetermined positions, and the valve members can be removed from the body and reinstalled in reversed positions to provide fixed communication between certain of the passageways. Resilient sleeves are inserted between the valve members and the manifold body to provide fluid tight seals, and externally threaded nipples on the edges of the body can receive a variety of fittings for connecting flow lines to the manifold assembly. An integral mounting bracket is provided in one embodiment for mounting the assembly on a support.

It is in general an object of the invention to provide a new and improved manifold assembly for medical applications.

Another object of the invention is to provide a manifold assembly of the above character which is fabricated of plastic.

Another object of the invention is to provide a manifold assembly of the above character which is inexpensive to manufacture and reliable and durable in use.

Additional objects and features of the invention will be apparent from the following description in which the preferred embodiments are set forth in detail in conjunction with the accompanying drawings.

BRIEF DESCRIPTION OF THE DRAWINGS

FIG. 1 is a top plan view of one embodiment of a manifold assembly according to the invention.

FIG. 2 is a cross-sectional view taken along line 2—2 in FIG. 1.

FIG. 3 is a cross-sectional view taken along line 3—3 in FIG. 1.

FIG. 4 is a cross-sectional view taken along line 4—4 in FIG. 1.

FIG. 5 is a cross-sectional view taken along line 5—5 in FIG. 4.

FIG. 6 is a cross-sectional view taken along line 6—6 in FIG. 1.

FIG. 7 is an exploded perspective view illustrating the addition of a bottom cover plate and a mounting bracket to the manifold assembly of FIGS. 1-6, with the valve members omitted for clarity of illustration.

FIG. 8 is a perspective view of a valve member used in the manifold assembly of the invention.

FIG. 9 is a top plan view of a second embodiment of a manifold assembly according to the invention, with the valve members removed for clarity of illustration.

FIG. 10 is a cross-sectional view taken along line 10—10 in FIG. 9.

FIG. 11 is a cross-sectional view taken along line 11—11 in FIG. 9.

FIG. 12 is a cross-sectional view taken along line 12—12 in FIG. 9.

FIG. 13 is a bottom plan view of the manifold assembly of FIGS. 9-12.

FIG. 14 is a bottom plan view of another embodiment of a manifold assembly according to the invention.

FIG. 15 is a sectional view taken along line 15—15 in FIG. 14.

FIG. 16 is a sectional view taken along line 16—16 in FIG. 14.

FIG. 17 is an end view of the manifold assembly of FIG. 14.

FIG. 18 is a bottom plan view of another embodiment of a manifold assembly according to the invention.

FIG. 19 is an end view of the embodiment of FIG. 18.

FIG. 20 is an enlarged fragmentary cross sectional view taken along line 20—20 in FIG. 18.

FIG. 21 is a fragmentary cross sectional view taken along line 21—21 in FIG. 20.

FIG. 22 is a cross sectional view taken along line 22—22 in FIG. 20.

DESCRIPTION OF THE PREFERRED EMBODIMENTS

The manifold assembly illustrated in FIGS. 1-7 includes a generally rectangular hollow body 21 having a top wall 22, side walls 23, 24 and end walls 26, 27. A centrally disposed rib 31 extends longitudinally of the body and has an axially extending flow passageway 32 formed therein. This passageway extends through ends walls 26, 27 and externally threaded nipples 33, 34 on the ends of the body. Additional ribs 36-40 extend laterally of the manifold body and intersect rib 31. Flow passageways 42-46 extend axially of ribs 36-40 and pass through side wall 23 and externally threaded nipples 42-46 on the side of the manifold body.

Cylindrical bosses 57-61 are provided at the intersections of the ribs, and bores 63-67 formed in the bosses open through top wall 22. The bores intersect the passageways and extend in a direction normal to them.

Valve means is provided for controlling communciation between the passageways in the manifold body. This means includes valve members 71-75 having cylindrical core portions 71a-75a rotatively mounted in bores 63-67, respectively. The valve members also include knobs 71b-75b affixed to the core portions and accessible externally of the manifold body. The core portions of the valves are provided with T-shaped passageways 71c-75c opening through the cylindrical side walls of the core portions. These passageways are adapted for alignment with different ones of the passageways in the manifold body depending upon the rotative positions of the valve members. The knobs are provided with arrows 77 which are in general aligned with the T-shaped passageways and serve to indicate the positions of these passageways.

Means is provided for limiting the rotation of the valve members between predetermined positions. This means includes pins 81–85 which extend from top wall 22 of the manifold body and arcuate stop members 71d–75d carried by the valve members. The stop members have radially extending faces 87, 88 and notches 89 for engaging the pins to limit the rotation of the valve members. The valve members are removably mounted in the manifold body, and they can be installed either with the pins between faces 87 and 88 or with the pins in notches 89. With the pin installed between faces 87 and 88, the valve member is free to rotate between the limiting positions defined by the faces. When the valve member is installed in the reverse position, i.e. with the pin in the notch, the valve member is oriented in a predetermined position and constrained against rotation.

The manifold body has additional bosses 91–94 in which openings 96–99 are formed. These openings open through top wall 22 and are adapted to receive the locating pins 101, 102 of a mounting bracket 103. This bracket is preferably of the type described in the aforementioned U.S. Pat. No. 3,447,469, and it is adapted to be mounted on a vertical rod such as the upright rod of a stand used in intravenous feeding. The bracket includes a support plate 104 which in use is generally oriented in a horizontal position with the manifold assembly resting on it. The angular position of the manifold assembly relative to the mounting bracket is determined by the holes in which pins 101, 102 are located.

If desired, the bottom of the hollow manifold body can be closed by a cover plate 106. As illustrated in FIG. 7, cover plate 106 is provided with openings 107 and 108 which are aligned respectively with bores 63–67 and openings 96–99. The cover plate is affixed to the manifold body by suitable means such as sonic welding or cementing. Pins 109, which are similar to pins 81–85, extend from the cover plate, and the valve members can be inserted from the cover plate side of the manifold, if desired.

Nipples 33–34 and 51–55 provide means for connecting flow lines to the manifold assembly, and they are adapted for receiving a number of different types of fittings for this purpose. Several such fittings are illustrated in FIG. 1, including a Luer fitting converter 111, sleeve clamps 112 and 113, and a one-twist male fitting 114. Fittings 111–113 have internal threads which engage the external threads of the nipples, and fitting 114 fits over a tapered portion of the nipples.

In the preferred embodiment, the manifold body is fabricated of a plastic such as polysulfone or a polycarbonate such as Lexan, and with the exception of cover plate 106 it is formed as a unitary structure by a suitable process such as injection molding. Other materials can be used, if desired, but the material used should preferably be one which can be cleaned by sterilizing. The valve members are fabricated of a suitable material such as teflon or fluorinated ethylene propylene, and they are machined to provide a fluid tight fit in bores 63–67.

Operation and use of the mainfold assembly of FIGS. 1–7 can be described briefly. The assembly is generally mounted in a horizontal position with top wall 22 facing up. Flow lines are connected to the nipples by suitable fittings, and valve members 71–75 are positioned to provide communication between desired ones of the flow lines via the passageways in the manifold body. For example, with valve member 77 in the position illustrated, passageway 42 is in communication with the inner portion of passageway 32 through T-shaped passageway 71c, and the outer portion of passageway 32 is isolated from the other passageways. If valve member 71 were rotated 90 degrees in the clockwise direction, as viewed in FIGS. 1 and 5, the inner and outer portions of passageway 32 would communicate through T-shaped passageway 71c, and passageway 42 would be isolated. If the valve member were then rotated an additional 90 degrees, passageway 42 would be in communication with the outer portion of passageway 32, and these passageways would be isolated from the remainder of the passageways. When a valve member is positioned with the pin in the notch, for example, as valve member 73 is positioned, the valve member is constrained against rotation, and the portions of passageway 32 on both sides of the valve member are in communication with the laterally extending passageway, e.g. passageway 44. For cleaning, the valve members can be removed from the body, and the body can be sterilized in the conventional manner.

The manifold assembly illustrated in FIGS. 9–13 includes a generally rectangular body, which in the preferred embodiment, is also molded as a unitary structure of a plastic such as polysulfone or a polycarbonate such as Lexan. This body is formed to include a longitudinally extending flow passageway 122 which opens through an externally threaded nipple 123 at one end of the body. The body is also formed to include laterally extending flow passageways 126–129 which lie in a common plane with passageway 122 and open through externally threaded nipples 131–134 at the sides of the body.

Cylindrical bosses 136–138 extend normally from body 121 at the intersections of the longitudinal and lateral passageways. Bores 141–143 extend through the bosses, and valve members of the type shown in FIG. 8 are rotatably mounted in these bores. Pins 146–148 extend from the body adjacent to bosses 136–138 and cooperate with the stop members of the valve members to limit the rotation of the valve members between predetermined positions.

Manifold body 121 is also provided with additional bosses 151–154 which define openings 156–159 for receiving the locating pins of a mounting bracket similar to bracket 103.

Operation and use of the manifold assembly of FIGS. 9–13 is generally similar to that described above in connection with the manifold assembly of FIGS. 1–7. The valve members control the communication between the passageways in the manifold body and the flow lines connected thereto. The arrangement of the valves and passageways in the assembly of FIGS. 9–13 make this unit particularily suitable for angiocardiographic work.

The manifold assembly illustrated in FIGS. 14–17 includes a generally planar body which, in the preferred embodiment, is molded as a unitary structure of a plastic such as Polysulfone or a polycarbonate such a Lexan. This body comprises a generally rectangular portion 221 having a top wall 222, side walls 223, 224, and end walls 226, 227. A centrally disposed rib 231 extends longitudinally of the rectangular body portion and has an axially extending flow passageway 232 formed therein. This passageway extends through end walls 226, 227 and externally threaded nipples 233, 234 at the ends of the body. Additional ribs 236–240 extend laterally of the manifold body and intersect rib 231. Flow passageways 242–246 extend axially of ribs 236–240 and pass through side wall 223 and externally threaded nipples 252–256 at the side of the manifold body.

Cylindrical bosses 257–261 are provided at the intersections of the ribs, and bores 263–267 formed in the bosses extend through top wall 222. The bores intersect the passageways and extend in a direction normal to them.

Communication between the passageways in the manifold body is controlled by valve members 271–275 which are similar to valve members 71–75. As in the embodiment of FIGS. 1–7, rotation of the valve members is limited by pins 281–285 which extend from top wall 222 and engage stops on the valve members.

The body of the manifold assembly of FIGS. 14–17 also includes a generally planar mounting flange 310 which extends laterally from side 224 of the generally rectangular portion. In the preferred embodiment, the mounting flange is formed integrally with the rectangular portion and includes a plate 311 which is aligned generally with top wall 222 of the rectangular portion. Depending skirts 312 and 313 extend along the side edges of plate 311 which are inclined outwardly, as illustrated in FIG. 14, and ribs 316 and 317 extend along the underside of plate 311 parallel to the skirts.

An outwardly facing flange 321 is provided at the outer edge of flange 311. Flange 311 forms an inwardly extending notch 322 adapted to receive a support member 323 such as the upright rod of an intravenous feeding stand. A rib 324 is spaced from and generally parallel to flange 321 on the underside of flange plate 311.

Threaded studs 326 and 327 extend laterally from the outer edge of mounting flange 311. These studs are anchored in bosses 328 and 329 on the mounting flange, and they are molded in place during the fabrication of the manifold body. The studs extend through suitable openings in a clamping bar 331, and wing nuts 332 and 333 provide means for drawing the clamping bar toward flange 321 to secure the assembly to support rod 323.

Operation and use of the manifold assembly of FIGS. 14–17 is similar to the operation and use of the embodiment of FIGS. 1–7.

The manifold assembly illustrated in FIGS. 18–22 includes a generally planar body which, in the preferred embodiment, is molded as a unitary structure of a rigid platic material such as a polycarbonate such as Lexan. This body comprises a generally rectangular portion 351 having a top wall 352, side walls 353, 354 and end walls 356, 357. A centrally disposed rib 358 extends longitudinally of the rectangular body portion and has an axially extending flow passageway 359 formed therein. This passageway extends through end walls 356, 357 and externally threaded nipples 361, 362 at the ends of the body. Additional ribs 363–367 extend laterally of the manifold body and intersect rib 358. Flow passageways 371–375 extend axially of ribs 363–367 and pass through side wall 353 and externally threaded nipples 377–381 at the side of the manifold body.

Cylindrical bosses 383–387 are provided at the intersections of the ribs, and bores 389–393 formed in the bosses extend through top wall 352. The bores intersect the passageways and extend in a direction normal to them.

Communication between the passageways in the manifold body is controlled by valve members 395–399 which are generally similar to valve members 71–75. However, instead of having T-shaped passageways, valve members 395–399 have generally semicircular arcuately extending peripheral passageways 395a–399a formed in the cylindrical core portions 395b–399b of the valve members. In the preferred embodiment, the valve members are fabricated of a rigid material such as polytetramethyle-terepthlate, polypropylene or polyethylene. As in the previous embodiments, rotation of the valve members is limited by pins 400 which extend from top wall 352 and engage stops on the valve members.

Valve members 395–399 are rotatively mounted in sleeves 401–405 inserted in bores 389–393. The sleeves are fabricated of a resilient material, such as polyurethane, which is softer than the valve members and valve body, and to provide fluid tight seals between the valve members and valve body, while permitting rotation of the valve members. The sleeves are provided with openings 401a,b,c–405a,b,c which are aligned with the passageways in the valve body. The sleeves are also provided with keys 401d–405d which are received in keyways 389a–393a in bores 389–393 to prevent rotation of the sleeves in the valve body. In the preferred embodiment, the sleeves are removably mounted in bores and the valve members are removably mounted in the sleeves.

The body of the manifold assembly of FIGS. 18–22 also includes a generally planar mounting flange 411 which extends laterally from side 354 of the generally rectangular portion. In the preferred embodiment, the mounting flange is formed integrally with the rectangular portion and includes a plate 412 which is aligned generally with top wall 352 of the rectangular portion. A depending skirt 413 extends along the periphery of the flange, and a grid work of ribs 414 provides additional rigidity for the flange. A V-shaped flanged notch 416 is formed in the flange and adapted to receive a support member 417 such as the upright rod of an intravenous feeding stand. A clamping screw 418 is threadedly mounted in the flange and aligned with the notch for engaging the side of the support opposite to the notch whereby the manifold assembly is clamped to the support.

Operation and use of the manifold assembly of FIGS. 18–22 is generally similar to the operation and use of the embodiments previously described.

Although not shown in the passageways, the flow passageways in all of the embodiments described above are tapered slightly so that they are somewhat larger in diameter at their outer ends than at their inner ends. This taper is formed during the molding process and facilitates separation of the manifold and molding tools.

The invention has a number of important features and advantages. Being made of plastic, the manifold assembly can be manufactured by a relatively inexpensive process, yet it has a reliability and durability comparable to more expensive stainless steel manifolds of the prior art. With the male fittings formed as an integral part of the manifold, there are no voids or gaps in the flow passageways to collect debris and the passageways can be cleaned easily and thoroughly. The use of the soft inserts between the valve members and valve body eliminates the need for machining to get a proper fit for the valve members and enables the entire assembly to be manufactured by a relatively inexpensive molding process. In addition, the plastic construction provides an electrically non-conductive structure within which physiological fluids are protected from stray electrical currents, thereby providing an additional measure of safety over manifolds constructed wholly or partly of metal or other electrically conductive materials.

It is apparent from the foregoing that a new and improved manifold assembly has been provided. While only the presently preferred embodiments have been described, as will be apparent to those familiar with the art, certain changes and modifications can be made without departing from the scope of the invention as defined by the following claims.

I claim:

1. In a manifold assembly: a generally planar body fabricated as a unitary structure of a substantially rigid plastic material including a longitudinally extending rib and a plurlity of laterally extending ribs intersecting the longitudinally extending rib, each of said ribs being formed to include an axially extending flow passageway, valve bores formed in the body at the intersections of the ribs and extending in a direction normal to the passageways, and valve members rotatively mounted in the bores for controlling communication between the passageways.

2. The manifold assembly of claim 1 ,urther including sleeves fabricated of a material softer than the valve members and mainfold body disposed between the valve members and the walls of the bores to form a seal between the same.

3. The manifold assembly of claim 1 further including stop means carried by the manifold body and valve members for limiting the rotation of the valve members between predetermined positions.

4. The manifold assembly of claim 1 wherein the manifold body is fabricated of molded plastic.

5. The manifold assembly of claim 1 further including a mounting flange extending laterally from one edge of the body and clamp means carried by the flange for mounting the assembly on a support, said flange and said body being substantially coplanar.

6. In a manifold assembly; a body of rigid plastic having a generally planar wall, longitudinally and laterally extending ribs on one side of said wall, axially extending flow passageways formed in the ribs, valve bores formed in the body at the intersections of the ribs and extending in a direction normal to the passageways, valve members rotatably mounted in the bores for controlling communication between the passageways, and sleeves fabricated of a material softer than the valve members and the manifold body disposed between the valve members and the walls of the bores to form a seal between the same.

7. The manifold assembly of claim 6 wherein the sleeves are constrained against rotation within the bores and the valve members are rotatably mounted in the sleeves.

8. In a manifold assembly; a body of rigid plastic having a generally planar wall, longitudinally and laterally extending ribs on one side of said wall, axially extending flow passageways formed in the ribs, valve bores formed in the body at the intersections of the ribs and extending in a direction normal to the passageways, valve members rotatably mounted in the bores for controlling communication between the passageways, and sleeves fabricated of a material softer than the valve members and the manifold body disposed between the valve members and the walls of the bores to form a seal between the same, said sleeves being inserted axially into the bores and including annular flange portions which abut against the outer face of the planar wall.

* * * * *